(12) United States Patent
Hagihara et al.

(10) Patent No.: US 6,403,355 B1
(45) Date of Patent: Jun. 11, 2002

(54) AMYLASES

(75) Inventors: Hiroshi Hagihara; Kaori Kitayama; Yasuhiro Hayashi; Kazuaki Igarashi; Keiji Endo; Katsuya Ozaki, all of Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/465,519

(22) Filed: Dec. 16, 1999

(30) Foreign Application Priority Data

Dec. 21, 1998 (JP) ............................................ 10-362487
Dec. 21, 1998 (JP) ............................................ 10-362488

(51) Int. Cl.[7] ............................. C12N 9/00; C12N 9/24; C12N 9/28; C12P 21/06
(52) U.S. Cl. ....................... 435/202; 435/183; 435/200; 435/201; 435/69.1
(58) Field of Search ......................... 510/392; 536/23.2, 536/23.7; 435/183, 200, 210, 69.1, 201, 202

(56) References Cited

FOREIGN PATENT DOCUMENTS

| WO | 9011352 | 10/1990 |
|----|---------|---------|
| WO | 9426881 | 11/1994 |
| WO | 9502639 | 1/1995 |
| WO | 9602633 | 2/1996 |

OTHER PUBLICATIONS

Mischa Machius et al, Activation of Bacillus licheniformis a–amylase through a disorder order transition of the substrate–binding site mediated by a calcium–sodium–calcium metal triad, Jan. 12, 1998.

Edited by Jan H. van Ee et al, Enzymes in Detergency, copyright 1997 by Marcel Dekker, Inc.

Edited by The Amylase Research Society of Japan, Handbook of Amylases and Related Enzymes, copyright 1988 by Pergamon Press.

Primary Examiner—Ponnathapu Achutamurthy
Assistant Examiner—Manjunath Rao
(74) Attorney, Agent, or Firm—Birch, Stewart, Kolasch & Birch, LLP

(57) ABSTRACT

Described are liquefying alkaline amylases each having residual activity not less than 70% when treated at pH 10 and 45° C. for 30 minutes in the presence of 1 to 100 mM of EDTA or EGTA; and a detergent comprising the same. Compared with the conventional amylases for a detergent, they have high chelating-agent resisting performance.

10 Claims, 6 Drawing Sheets

FIG. 1: EDTA-RESISTING PERFORMANCE

FIG. 2: EGTA-RESISTING PERFORMANCE

Acting pH of K36

Acting pH of K38

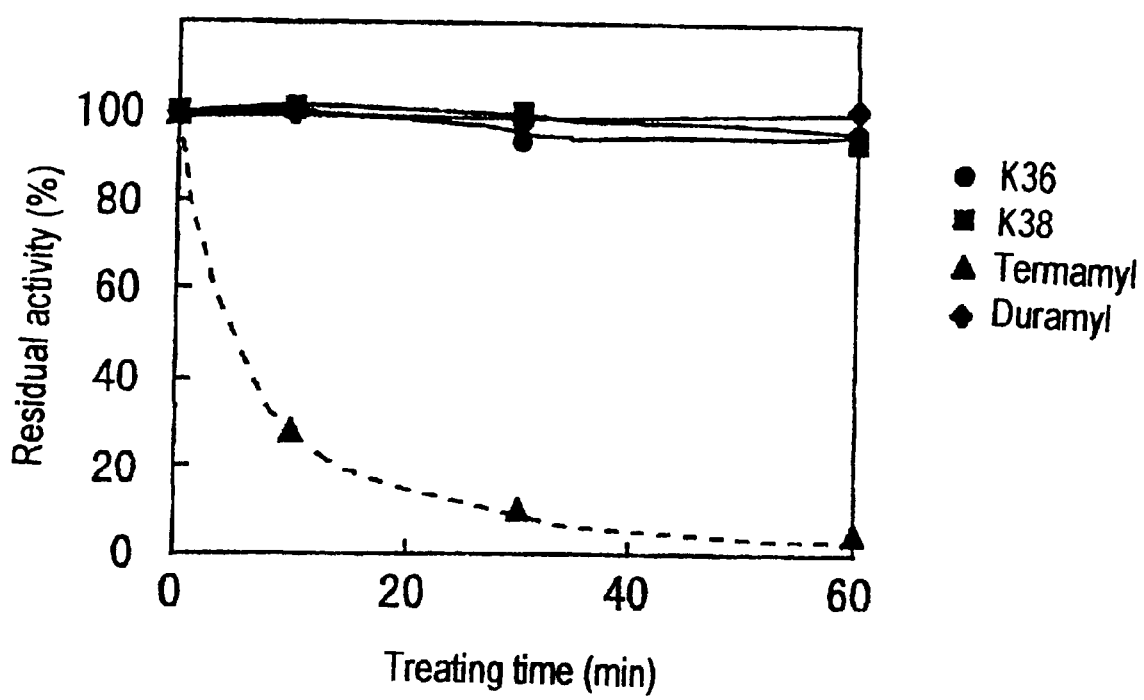
FIG. 9: OXIDIZING-AGENT-RESISTING PERFORMANCE

SEQUENCE LISTING

<160> NUMBER OF SEQ ID NOS: 7

<210> SEQ ID NO 1
<211> LENGTH: 1650
<212> TYPE: DNA
<213> ORGANISM: Bacillus sp.
<220> FEATURE:
<221> NAME/KEY: CDS
<222> LOCATION: (65)..(1567)

<400> SEQUENCE: 1

```
cttgaatcat tatttaaagc tggttatgat atatgtaagc gttatcatta a aaggaggta      60 tttg atg aaa aga tgg gta gta gca atg ctg gca gtg tta ttt tta ttt     109
     Met Lys Arg Trp Val Val Ala Me t Leu Ala Val Leu Phe Leu Phe
     1               5                  10                  15 cct tcg gta gta gtt gca gat ggc ttg aat g ga acg atg atg cag tat     157
Pro Ser Val Val Val Ala Asp Gly Leu Asn G ly Thr Met Met Gln Tyr
            20                  25                  30 tat gag tgg cat cta gag aat gat ggg caa c ac tgg aat cgg ttg cat     205
```

```
                Tyr Glu Trp His Leu Glu Asn Asp Gly Gln His Trp Asn Arg Leu His
                             35                  40                  45 gat gat gcc gaa gct tta agt aat gcg ggt att aca gct att tgg ata              253
Asp Asp Ala Glu Ala Leu Ser Asn Ala Gly Ile Thr Ala Ile Trp Ile
         50                  55                  60 ccc cca gcc tac aaa gga aat agt cag gct gat gtt ggg tat ggt gca              301
Pro Pro Ala Tyr Lys Gly Asn Ser Gln Ala Asp Val Gly Tyr Gly Ala
 65                  70                  75 tac gac ctt tat gat tta ggg gag ttt aat caa aaa ggt acc gtt cga              349
Tyr Asp Leu Tyr Asp Leu Gly Glu Phe Asn Gln Lys Gly Thr Val Arg
 80                  85                  90                  95 acg aaa tac ggg aca aag gct cag ctt gag cga gct ata ggg tcc cta              397
Thr Lys Tyr Gly Thr Lys Ala Gln Leu Glu Arg Ala Ile Gly Ser Leu
                    100                 105                 110 aag tcg aat gat atc aat gtt tat ggg gat gtc gta atg aat cat aaa              445
Lys Ser Asn Asp Ile Asn Val Tyr Gly Asp Val Val Met Asn His Lys
                115                 120                 125 tta gga gct gat ttc acg gag gca gtg caa gct gtt caa gta aat cct              493
Leu Gly Ala Asp Phe Thr Glu Ala Val Gln Ala Val Gln Val Asn Pro
            130                 135                 140 tcg aac cgt tgg cag gat att tca ggt gtc tac acg att gat gca tgg              541
Ser Asn Arg Trp Gln Asp Ile Ser Gly Val Tyr Thr Ile Asp Ala Trp
        145                 150                 155 acg gga ttt gac ttt cca ggg cgc aac aat gcc tat tcc gat ttt aaa              589
Thr Gly Phe Asp Phe Pro Gly Arg Asn Asn Ala Tyr Ser Asp Phe Lys
160                 165                 170                 175 tgg aga tgg ttc cat ttt aat ggc gtt gac tgg gat caa cgc tat caa              637
Trp Arg Trp Phe His Phe Asn Gly Val Asp Trp Asp Gln Arg Tyr Gln
                    180                 185                 190 gaa aac cat ctt ttt cgc ttt gca aat acg aac tgg aac tgg cga gtg              685
Glu Asn His Leu Phe Arg Phe Ala Asn Thr Asn Trp Asn Trp Arg Val
                195                 200                 205 gat gaa gag aat ggt aat tat gac tat tta tta gga tcg aac att gac              733
Asp Glu Glu Asn Gly Asn Tyr Asp Tyr Leu Leu Gly Ser Asn Ile Asp
            210                 215                 220 ttt agc cac cca gag gtt caa gag gaa tta aag gat tgg ggg agc tgg              781
Phe Ser His Pro Glu Val Gln Glu Glu Leu Lys Asp Trp Gly Ser Trp
        225                 230                 235 ttt acg gat gag cta gat tta gat ggg tat cga ttg gat gct att aag              829
Phe Thr Asp Glu Leu Asp Leu Asp Gly Tyr Arg Leu Asp Ala Ile Lys
240                 245                 250                 255 cat att cca ttc tgg tat acg tca gat tgg gtt agg cat cag cga agt              877
His Ile Pro Phe Trp Tyr Thr Ser Asp Trp Val Arg His Gln Arg Ser
                    260                 265                 270 gaa gca gac caa gat tta ttt gtc gta ggg gag tat tgg aag gat gac              925
Glu Ala Asp Gln Asp Leu Phe Val Val Gly Glu Tyr Trp Lys Asp Asp
                275                 280                 285 gta ggt gct ctc gaa ttt tat tta gat gaa atg aat tgg gag atg tct              973
Val Gly Ala Leu Glu Phe Tyr Leu Asp Glu Met Asn Trp Glu Met Ser
            290                 295                 300 cta ttc gat gtt ccg ctc aat tat aat ttt tac cgg gct tca aag caa             1021
Leu Phe Asp Val Pro Leu Asn Tyr Asn Phe Tyr Arg Ala Ser Lys Gln
        305                 310                 315 ggc gga agc tat gat atg cgt aat att tta cga gga tct tta gta gaa             1069
Gly Gly Ser Tyr Asp Met Arg Asn Ile Leu Arg Gly Ser Leu Val Glu
320                 325                 330                 335 gca cat ccg att cat gca gtt acg ttt gtt gat aat cat gat act cag             1117
Ala His Pro Ile His Ala Val Thr Phe Val Asp Asn His Asp Thr Gln
                    340                 345                 350
```

```
cca gga gag tca tta gaa tca tgg gtc gct g at tgg ttt aag cca ctt      1165
Pro Gly Glu Ser Leu Glu Ser Trp Val Ala A sp Trp Phe Lys Pro Leu
            355                 360                 365 gct tat gcg aca atc ttg acg cgt gaa ggt g gt tat cca aat gta ttt      1213
Ala Tyr Ala Thr Ile Leu Thr Arg Glu Gly G ly Tyr Pro Asn Val Phe
            370                 375                 380 tac ggt gac tac tat ggg att cct aac gat a ac att tca gct aag aag     1261
Tyr Gly Asp Tyr Tyr Gly Ile Pro Asn Asp A sn Ile Ser Ala Lys Lys
385                 390                 395 gat atg att gat gag ttg ctt gat gca cgt c aa aat tac gca tat ggc     1309
Asp Met Ile Asp Glu Leu Leu Asp Ala Arg G ln Asn Tyr Ala Tyr Gly
400                 405                 410                 415 aca caa cat gac tat ttt gat cat tgg gat a tc gtt gga tgg aca aga    1357
Thr Gln His Asp Tyr Phe Asp His Trp Asp I le Val Gly Trp Thr Arg
            420                 425                 430 gaa ggt aca tcc tca cgt cct aat tcg ggt c tt gct act att atg tcc    1405
Glu Gly Thr Ser Ser Arg Pro Asn Ser Gly L eu Ala Thr Ile Met Ser
            435                 440                 445 aat ggt cct gga gga tca aaa tgg atg tac g ta gga cag caa cat gca    1453
Asn Gly Pro Gly Gly Ser Lys Trp Met Tyr V al Gly Gln Gln His Ala
            450                 455                 460 gga caa acg tgg aca gat tta act ggc aat c ac gcg gcg tcg gtt acg    1501
Gly Gln Thr Trp Thr Asp Leu Thr Gly Asn H is Ala Ala Ser Val Thr
465                 470                 475 att aat ggt gat ggc tgg ggc gaa ttc ttt a ca aat gga gga tct gta    1549
Ile Asn Gly Asp Gly Trp Gly Glu Phe Phe T hr Asn Gly Gly Ser Val
480                 485                 490                 495 tcc gtg tat gtg aac caa taataaaaag ccttgagaag g gattcctcc            1597
Ser Val Tyr Val Asn Gln
                500 ctaactcaag gctttcttta tgtcgtttag ctcaacgctt ctacgaagct t ta           1650

<210> SEQ ID NO 2
<211> LENGTH: 501
<212> TYPE: PRT
<213> ORGANISM: Bacillus sp.

<400> SEQUENCE: 2

Met Lys Arg Trp Val Val Ala Met Leu Ala V al Leu Phe Leu Phe Pro
1               5                   10                  15

Ser Val Val Ala Asp Gly Leu Asn Gly T hr Met Met Gln Tyr Tyr
            20                  25                  30

Glu Trp His Leu Glu Asn Asp Gly Gln His T rp Asn Arg Leu His Asp
        35                  40                  45

Asp Ala Glu Ala Leu Ser Asn Ala Gly Ile T hr Ala Ile Trp Ile Pro
    50                  55                  60

Pro Ala Tyr Lys Gly Asn Ser Gln Ala Asp V al Gly Tyr Gly Ala Tyr
65                  70                  75                  80

Asp Leu Tyr Asp Leu Gly Glu Phe Asn Gln L ys Gly Thr Val Arg Thr
                85                  90                  95

Lys Tyr Gly Thr Lys Ala Gln Leu Glu Arg A la Ile Gly Ser Leu Lys
            100                 105                 110

Ser Asn Asp Ile Asn Val Tyr Gly Asp Val V al Met Asn His Lys Leu
        115                 120                 125

Gly Ala Asp Phe Thr Glu Ala Val Gln Ala V al Gln Val Asn Pro Ser
    130                 135                 140

Asn Arg Trp Gln Asp Ile Ser Gly Val Tyr T hr Ile Asp Ala Trp Thr
145                 150                 155                 160
```

```
Gly Phe Asp Phe Pro Gly Arg Asn Asn Ala Tyr Ser Asp Phe Lys Trp
                165                 170                 175

Arg Trp Phe His Phe Asn Gly Val Asp Trp Asp Gln Arg Tyr Gln Glu
            180                 185                 190

Asn His Leu Phe Arg Phe Ala Asn Thr Asn Trp Asn Trp Arg Val Asp
        195                 200                 205

Glu Glu Asn Gly Asn Tyr Asp Tyr Leu Leu Gly Ser Asn Ile Asp Phe
    210                 215                 220

Ser His Pro Glu Val Gln Glu Leu Lys Asp Trp Gly Ser Trp Phe
225                 230                 235                 240

Thr Asp Glu Leu Asp Leu Asp Gly Tyr Arg Leu Asp Ala Ile Lys His
                245                 250                 255

Ile Pro Phe Trp Tyr Thr Ser Asp Trp Val Arg His Gln Arg Ser Glu
                260                 265                 270

Ala Asp Gln Asp Leu Phe Val Val Gly Glu Tyr Trp Lys Asp Asp Val
                275                 280                 285

Gly Ala Leu Glu Phe Tyr Leu Asp Glu Met Asn Trp Glu Met Ser Leu
            290                 295                 300

Phe Asp Val Pro Leu Asn Tyr Asn Phe Tyr Arg Ala Ser Lys Gln Gly
305                 310                 315                 320

Gly Ser Tyr Asp Met Arg Asn Ile Leu Arg Gly Ser Leu Val Glu Ala
                325                 330                 335

His Pro Ile His Ala Val Thr Phe Val Asp Asn His Asp Thr Gln Pro
                340                 345                 350

Gly Glu Ser Leu Glu Ser Trp Val Ala Asp Trp Phe Lys Pro Leu Ala
            355                 360                 365

Tyr Ala Thr Ile Leu Thr Arg Glu Gly Gly Tyr Pro Asn Val Phe Tyr
370                 375                 380

Gly Asp Tyr Tyr Gly Ile Pro Asn Asp Asn Ile Ser Ala Lys Lys Asp
385                 390                 395                 400

Met Ile Asp Glu Leu Leu Asp Ala Arg Gln Asn Tyr Ala Tyr Gly Thr
                405                 410                 415

Gln His Asp Tyr Phe Asp His Trp Asp Ile Val Gly Trp Thr Arg Glu
                420                 425                 430

Gly Thr Ser Ser Arg Pro Asn Ser Gly Leu Ala Thr Ile Met Ser Asn
            435                 440                 445

Gly Pro Gly Gly Ser Lys Trp Met Tyr Val Gly Gln Gln His Ala Gly
            450                 455                 460

Gln Thr Trp Thr Asp Leu Thr Gly Asn His Ala Ala Ser Val Thr Ile
465                 470                 475                 480

Asn Gly Asp Gly Trp Gly Glu Phe Phe Thr Asn Gly Gly Ser Val Ser
                485                 490                 495

Val Tyr Val Asn Gln
            500

<210> SEQ ID NO 3
<211> LENGTH: 1745
<212> TYPE: DNA
<213> ORGANISM: Bacillus sp.
<220> FEATURE:
<221> NAME/KEY: CDS
<222> LOCATION: (190)..(1692)

<400> SEQUENCE: 3
aactaagtaa catcgattca ggataaaagt atgcgaaacg atgcgcaaaa c tgcgcaact    60
```

| | |
|---|---:|
| actagcactc ttcagggact aaaccacctt ttttccaaaa atgacatcat a taaacaaat | 120 |
| ttgtctacca atcactattt aaagctgttt atgatatatg taagcgttat c attaaaagg | 180 |

```
aggtatttg atg aga aga tgg gta gta gca atg tt g gca gtg tta ttt tta    231
          Met Arg Arg Trp Val Val Ala Met Leu Ala Val Leu Phe Leu
           1               5               10 ttt cct tcg gta gta gtt gca gat gga ttg a ac ggt acg atg atg cag    279
Phe Pro Ser Val Val Val Ala Asp Gly Leu A sn Gly Thr Met Met Gln
 15              20              25               30 tat tat gag tgg cat ttg gaa aac gac ggg c ag cat tgg aat cgg ttg    327
Tyr Tyr Glu Trp His Leu Glu Asn Asp Gly G ln His Trp Asn Arg Leu
             35              40                 45 cac gat gat gcc gca gct ttg agt gat gct g gt att aca gct att tgg    375
His Asp Asp Ala Ala Ala Leu Ser Asp Ala G ly Ile Thr Ala Ile Trp
         50              55                 60 att ccg cca gcc tac aaa ggt aat agt cag g cg gat gtt ggg tac ggt    423
Ile Pro Pro Ala Tyr Lys Gly Asn Ser Gln A la Asp Val Gly Tyr Gly
             65              70                 75 gca tac gat ctt tat gat tta gga gag ttc a at caa aag ggt act gtt    471
Ala Tyr Asp Leu Tyr Asp Leu Gly Glu Phe A sn Gln Lys Gly Thr Val
 80              85                  90 cga acg aaa tac gga act aag gca cag ctt g aa cga gct att ggg tcc    519
Arg Thr Lys Tyr Gly Thr Lys Ala Gln Leu G lu Arg Ala Ile Gly Ser
 95              100                 105              110 ctt aaa tct aat gat atc aat gta tac gga g at gtc gtg atg aat cat    567
Leu Lys Ser Asn Asp Ile Asn Val Tyr Gly A sp Val Val Met Asn His
             115              120                125 aaa atg gga gct gat ttt acg gag gca gtg c aa gct gtt caa gta aat    615
Lys Met Gly Ala Asp Phe Thr Glu Ala Val G ln Ala Val Gln Val Asn
             130             135                 140 cca acg aat cgt tgg cag gat att tca ggt g cc tac acg att gat gcg    663
Pro Thr Asn Arg Trp Gln Asp Ile Ser Gly A la Tyr Thr Ile Asp Ala
             145             150                 155 tgg acg ggt ttc gac ttt tca ggg cgt aac a ac gcc tat tca gat ttt    711
Trp Thr Gly Phe Asp Phe Ser Gly Arg Asn A sn Ala Tyr Ser Asp Phe
 160             165                 170 aag tgg aga tgg ttc cat ttt aat ggt gtt g ac tgg gat cag cgc tat    759
Lys Trp Arg Trp Phe His Phe Asn Gly Val A sp Trp Asp Gln Arg Tyr
175             180                 185                 190 caa gaa aat cat att ttc cgc ttt gca aat a cg aac tgg aac tgg cga    807
Gln Glu Asn His Ile Phe Arg Phe Ala Asn T hr Asn Trp Asn Trp Arg
             195             200                 205 gtg gat gaa gag aac ggt aat tat gat tac c tg tta gga tcg aat atc    855
Val Asp Glu Glu Asn Gly Asn Tyr Asp Tyr L eu Leu Gly Ser Asn Ile
             210             215                 220 gac ttt agt cat cca gaa gta caa gat gag t tg aag gat tgg ggt agc    903
Asp Phe Ser His Pro Glu Val Gln Asp Glu L eu Lys Asp Trp Gly Ser
             225             230                 235 tgg ttt acc gat gag tta gat ttg gat ggt t at cgt tta gat gct att    951
Trp Phe Thr Asp Glu Leu Asp Leu Asp Gly T yr Arg Leu Asp Ala Ile
 240             245                 250 aaa cat att cca ttc tgg tat aca tct gat t gg gtt cgg cat cag cgc    999
Lys His Ile Pro Phe Trp Tyr Thr Ser Asp T rp Val Arg His Gln Arg
255             260                 265                 270 aac gaa gca gat caa gat tta ttt gtc gta g gg gaa tat tgg aag gat   1047
Asn Glu Ala Asp Gln Asp Leu Phe Val Val G ly Glu Tyr Trp Lys Asp
             275             280                 285
```

-continued

```
gac gta ggt gct ctc gaa ttt tat tta gat g aa atg aat tgg gag atg      1095
Asp Val Gly Ala Leu Glu Phe Tyr Leu Asp G lu Met Asn Trp Glu Met
                290                 295                 300 tct cta ttc gat gtt cca ctt aat tat aat t tt tac cgg gct tca caa      1143
Ser Leu Phe Asp Val Pro Leu Asn Tyr Asn P he Tyr Arg Ala Ser Gln
            305                 310                 315 caa ggt gga agc tat gat atg cgt aat att t ta cga gga tct tta gta      1191
Gln Gly Gly Ser Tyr Asp Met Arg Asn Ile L eu Arg Gly Ser Leu Val
        320                 325                 330 gaa gcg cat ccg atg cat gca gtt acg ttt g tt gat aat cat gat act      1239
Glu Ala His Pro Met His Ala Val Thr Phe V al Asp Asn His Asp Thr
335                 340                 345                 350 cag cca ggg gag tca tta gag tca tgg gtt g ct gat tgg ttt aag cca      1287
Gln Pro Gly Glu Ser Leu Glu Ser Trp Val A la Asp Trp Phe Lys Pro
                355                 360                 365 ctt gct tat gcg aca att ttg acg cgt gaa g gt ggt tat cca aat gta      1335
Leu Ala Tyr Ala Thr Ile Leu Thr Arg Glu G ly Gly Tyr Pro Asn Val
            370                 375                 380 ttt tac ggt gat tac tat ggg att cct aac g at aac att tca gct aaa      1383
Phe Tyr Gly Asp Tyr Tyr Gly Ile Pro Asn A sp Asn Ile Ser Ala Lys
        385                 390                 395 aaa gat atg att gat gag ctg ctt gat gca c gt caa aat tac gca tat      1431
Lys Asp Met Ile Asp Glu Leu Leu Asp Ala A rg Gln Asn Tyr Ala Tyr
400                 405                 410 ggc acg cag cat gac tat ttt gat cat tgg g at gtt gta gga tgg act      1479
Gly Thr Gln His Asp Tyr Phe Asp His Trp A sp Val Val Gly Trp Thr
                415                 420                 425                 430 agg gaa gga tct tcc tcc aga cct aat tca g gc ctt gcg act att atg      1527
Arg Glu Gly Ser Ser Ser Arg Pro Asn Ser G ly Leu Ala Thr Ile Met
                    435                 440                 445 tcg aat gga cct ggt ggt tcc aag tgg atg t at gta gga cgt cag aat      1575
Ser Asn Gly Pro Gly Gly Ser Lys Trp Met T yr Val Gly Arg Gln Asn
                450                 455                 460 gca gga caa aca tgg aca gat tta act ggt a at aac gga gcg tcc gtt      1623
Ala Gly Gln Thr Trp Thr Asp Leu Thr Gly A sn Asn Gly Ala Ser Val
                465                 470                 475 aca att aat ggc gat gga tgg ggc gaa ttc t tt acg aat gga gga tct      1671
Thr Ile Asn Gly Asp Gly Trp Gly Glu Phe P he Thr Asn Gly Gly Ser
            480                 485                 490 gta tcc gtg tac gtg aac caa taacaaaaag ccttgaga ag ggattcctcc         1722
Val Ser Val Tyr Val Asn Gln
495                 500 ctaactcaag gctttctttta tgt                                             1745
```

<210> SEQ ID NO 4
<211> LENGTH: 501
<212> TYPE: PRT
<213> ORGANISM: Bacillus sp.

<400> SEQUENCE: 4

```
Met Arg Arg Trp Val Val Ala Met Leu Ala V al Leu Phe Leu Phe Pro
  1               5                  10                  15

Ser Val Val Val Ala Asp Gly Leu Asn Gly T hr Met Met Gln Tyr Tyr
             20                  25                  30

Glu Trp His Leu Glu Asn Asp Gly Gln His T rp Asn Arg Leu His Asp
         35                  40                  45

Asp Ala Ala Leu Ser Asp Ala Gly Ile Thr A la Ile Trp Ile Pro
     50                  55                  60
```

```
Pro Ala Tyr Lys Gly Asn Ser Gln Ala Asp Val Gly Tyr Gly Ala Tyr
 65                  70                  75                  80

Asp Leu Tyr Asp Leu Gly Glu Phe Asn Gln Lys Gly Thr Val Arg Thr
                 85                  90                  95

Lys Tyr Gly Thr Lys Ala Gln Leu Glu Arg Ala Ile Gly Ser Leu Lys
            100                 105                 110

Ser Asn Asp Ile Asn Val Tyr Gly Asp Val Met Asn His Lys Met
        115                 120                 125

Gly Ala Asp Phe Thr Glu Ala Val Gln Ala Val Gln Val Asn Pro Thr
        130                 135                 140

Asn Arg Trp Gln Asp Ile Ser Gly Ala Tyr Thr Ile Asp Ala Trp Thr
145                 150                 155                 160

Gly Phe Asp Phe Ser Gly Arg Asn Asn Ala Tyr Ser Asp Phe Lys Trp
                165                 170                 175

Arg Trp Phe His Phe Asn Gly Val Asp Trp Asp Gln Arg Tyr Gln Glu
                180                 185                 190

Asn His Ile Phe Arg Phe Ala Asn Thr Asn Trp Asn Trp Arg Val Asp
            195                 200                 205

Glu Glu Asn Gly Asn Tyr Asp Tyr Leu Leu Gly Ser Asn Ile Asp Phe
            210                 215                 220

Ser His Pro Glu Val Gln Asp Glu Leu Lys Asp Trp Gly Ser Trp Phe
225                 230                 235                 240

Thr Asp Glu Leu Asp Leu Asp Gly Tyr Arg Leu Asp Ala Ile Lys His
                245                 250                 255

Ile Pro Phe Trp Tyr Thr Ser Asp Trp Val Arg His Gln Arg Asn Glu
                260                 265                 270

Ala Asp Gln Asp Leu Phe Val Val Gly Glu Tyr Trp Lys Asp Asp Val
            275                 280                 285

Gly Ala Leu Glu Phe Tyr Leu Asp Glu Met Asn Trp Glu Met Ser Leu
            290                 295                 300

Phe Asp Val Pro Leu Asn Tyr Asn Phe Tyr Arg Ala Ser Gln Gln Gly
305                 310                 315                 320

Gly Ser Tyr Asp Met Arg Asn Ile Leu Arg Gly Ser Leu Val Glu Ala
                325                 330                 335

His Pro Met His Ala Val Thr Phe Val Asp Asn His Asp Thr Gln Pro
            340                 345                 350

Gly Glu Ser Leu Glu Ser Trp Val Ala Asp Trp Phe Lys Pro Leu Ala
            355                 360                 365

Tyr Ala Thr Ile Leu Thr Arg Glu Gly Gly Tyr Pro Asn Val Phe Tyr
370                 375                 380

Gly Asp Tyr Tyr Gly Ile Pro Asn Asp Asn Ile Ser Ala Lys Lys Asp
                385                 390                 395                 400

Met Ile Asp Glu Leu Leu Asp Ala Arg Gln Asn Tyr Ala Tyr Gly Thr
                405                 410                 415

Gln His Asp Tyr Phe Asp His Trp Asp Val Val Gly Trp Thr Arg Glu
            420                 425                 430

Gly Ser Ser Ser Arg Pro Asn Ser Gly Leu Ala Thr Ile Met Ser Asn
            435                 440                 445

Gly Pro Gly Gly Ser Lys Trp Met Tyr Val Gly Arg Gln Asn Ala Gly
        450                 455                 460

Gln Thr Trp Thr Asp Leu Thr Gly Asn Asn Gly Ala Ser Val Thr Ile
465                 470                 475                 480
```

-continued

```
Asn Gly Asp Gly Trp Gly Glu Phe Phe Thr A sn Gly Gly Ser Val Ser
                485                 490                 495

Val Tyr Val Asn Gln
            500

<210> SEQ ID NO 5
<211> LENGTH: 15
<212> TYPE: PRT
<213> ORGANISM: Bacillus sp.

<400> SEQUENCE: 5

Asp Gly Leu Asn Gly Thr Met Met Gln Tyr T yr Glu Trp His Leu
 1               5                  10                  15

<210> SEQ ID NO 6
<211> LENGTH: 6
<212> TYPE: PRT
<213> ORGANISM: Bacillus sp.

<400> SEQUENCE: 6

Met Gln Tyr Phe Glu Trp
 1               5

<210> SEQ ID NO 7
<211> LENGTH: 6
<212> TYPE: PRT
<213> ORGANISM: Bacillus sp.

<400> SEQUENCE: 7

Trp Phe Lys Pro Leu Tyr
 1               5
```

AMYLASES

TECHNICAL FIELD

The present invention relates to liquefying alkaline α-amylases having high chelating-agent-resisting performance and are useful as a component for detergents.

BACKGROUND ART

α-Amylases have been used widely in various industrial fields such as starch, brewing, fiber, pharmaceutical and food industries. Since they are known to be suited as one of the components of a detergent, they are incorporated even in an automatic dish washing detergent or a laundry detergent as a detergency reinforcing component (Enzymes in Detergency, p203, Marcel Dekker Inc., New York (1995)).

As liquefying α-amylases useful for a detergent and having the optimum effects on the alkaline side, those previously found by the present inventors and derived from the strain Bacillus sp. KSM-1378 (FERM BP-3048) are known. Recently, α-amylases having the optimum pH at around 8 to 9.5 are disclosed (WO95/2639). They resemble closely to those derived from the strain KSM-1378 in properties and structure.

In a detergent, a chelating agent such as phosphoric acid, citric acid or zeolite is incorporated to remove, from a washing liquid, cleansing-disturbing ions such as calcium ions. It has been known for long years that liquefying α-amylases require calcium ions for expressing their enzyme activity but such calcium ions are deactivated by the above-described chelating agent or a stronger chelating agent EDTA [HANDBOOK OF AMYLASES AND RELATED ENZYMES, p43, The Amylase Research Society Japan(1988)]. In recent days, it is reported that X-ray crystallographic analysis of the liquefying α-amylases known to date reveals that three calcium atoms exist in the molecule thereof and 13 amino acid residues are conserved with markedly high frequency [Structure, 6, 281(1998)].

Inhibition of enzyme activity by a chelating agent is also recognized in the above-described liquefying alkaline α-amylase derived from the strain Bacillus sp. KSM-1378 (FERM BP-3048) and sufficient effects of this α-amylase are not always exhibited when it is incorporated in an automatic dish washing detergent or laundry detergent. Liquefying α-amylases (Termamyl and Duramyl, products of Novo Nordisk A/S) derived from *Bacillus licheniformis,* which are most frequently employed as a component of an automatic dish washing detergent or laundry detergent, are also insufficient in chelating-agent-resisting performance.

Among the liquefying amylases known to date, a liquefying α-amylase (WO90/11352) derived from the strain belonging to Pyrococcus sp. and an α-amylase (WO96/02633) which is derived from the strain belonging to Sulfolobus sp. and is effective in the liquefying step of a starch are free from the influence from a chelating agent. These enzymes however have the optimum acting pH in a range of 4 to 6 and 2.5 to 4.5, respectively and do not act in the alkaline range so that they are not suited as a component of a detergent.

An object of the present invention is therefore to provide a liquefying alkaline α-amylase having higher chelating-agent-resisting performance than conventional amylases for a detergent and is useful as a component of a detergent; and a detergent composition having this liquefying alkaline α-amylase incorporated therein.

Disclosure of the Invention

In one aspect of the present invention, there is thus provided a liquefying alkaline amylase having residual activity not less than 70% when treated at pH 10 and 45° C. for 30 minutes in the presence of 1 to 100 mM of EDTA or EGTA.

In another aspect of the present invention, there is also provided a DNA fragment encoding said liquefying alkaline amylase.

In a further aspect of the present invention, there is also provided a detergent composition containing said liquefying alkaline amylase.

BRIEF DESCRIPTION OF THE DRAWINGS

FIG. 9 is a diagram illustrating a relationship between a treating time with $H_2O_2$ and residual activity, of each of the liquefying alkaline amylases (K36 and K38) according to the present invention and known amylases used for detergent.

BEST MODES FOR CARRYING OUT THE INVENTION

Figure 1:
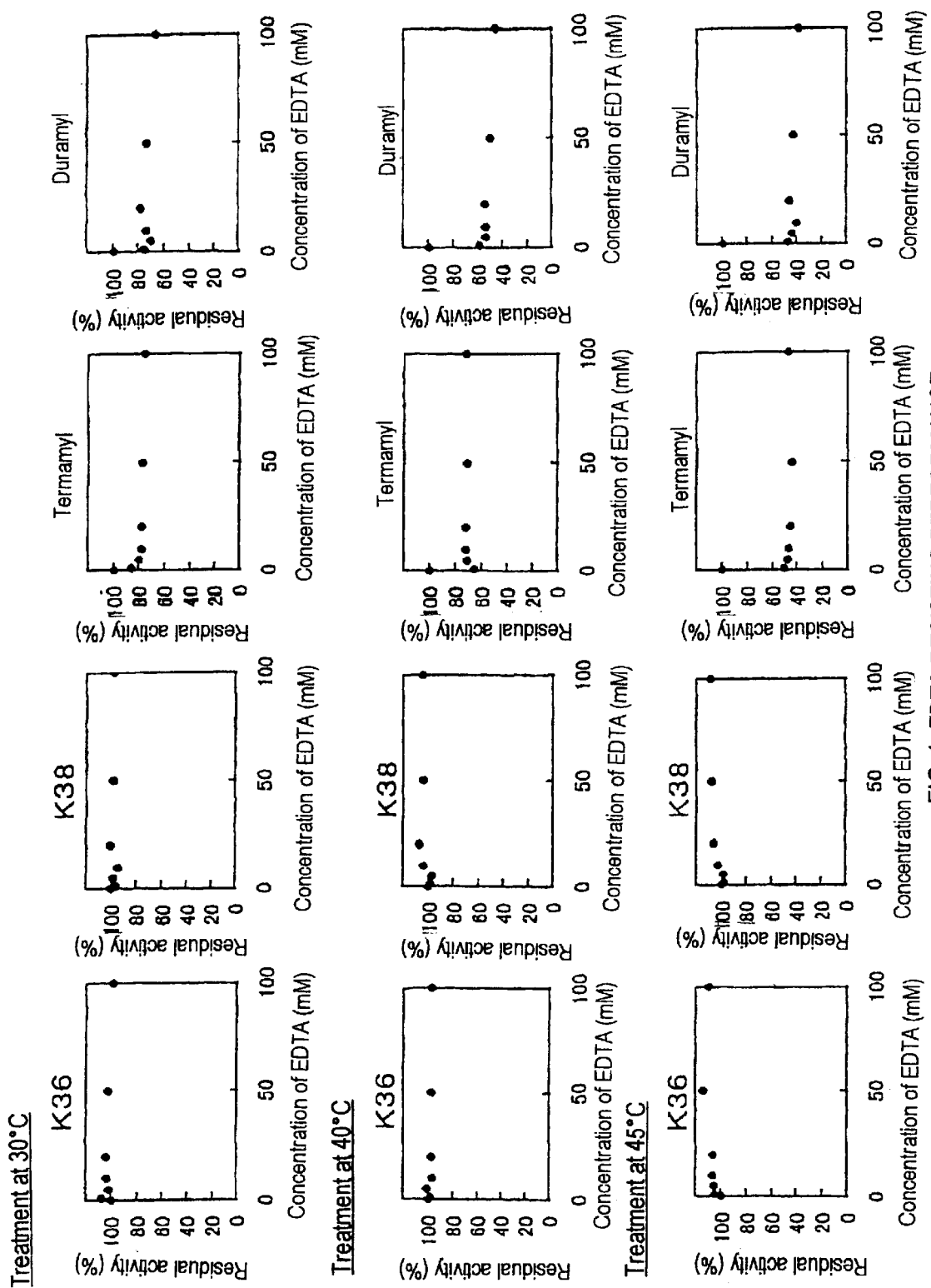
FIG. 1 is a diagram illustrating a relationship between a treating concentration with EDTA and residual activity, of the each of the liquefying alkaline amylases (K36 and K38) according to the present invention and known amylases used for a detergent.

The term "alkaline α-amylase" as used herein means an α-amylase having the optimum pH in the alkaline range. The term "neutral" as used herein means a pH range of from 6 to 8, while the term "alkaline" means a pH range higher than the neutral range. As described in HANDBOOK OF AMYLASES AND RELATED ENZYMES [p40–41, The Amylase Research Society of Japan(1988)], the term "liquefying α-amylase" means an α-amylase which degrades starches or starchy polysaccharides at high random.

The enzyme according to the present invention is a liquefying alkaline amylase having residual activity not less than 70% when treated at pH 10 and 45° C. for 30 minutes in the presence of 1 to 100 mM of EDTA or EGTA, with the residual activity not less than 80% being preferred and that not less than 90% being more preferred.

The invention enzyme is required to have the above-described chelating-agent resistance, but is preferred to have the below-described properties 1) and 2) and is more preferred to have the below-described properties 1 to 5).

1) Optimum Acting pH

It has optimum action at pH exceeding 8.0 (as a result of reaction at 50° C. for 15 minutes with a soluble starch as a substrate)

2) Action

It hydrolyzes α-1,4-glucosidic linkages in starches, amylose, amylopectin and partial degradation products thereof and from amylose, forms glucose (G1), maltose (G2), maltotriose (G3), maltotetraose (G4), maltopentaose (G5), maltohexaose (G6) and maltoheptaose (G7). It however does not act on pullulan.

3) pH Stability (Britton-Robinson Buffer)

It exhibits residual activity not less than 70% within a pH range of from 6.5 to 11.0 when treated at 40° C. for 30 minutes.

4) Acting Temperature Range and Optimum Acting Temperature

It acts in a wide temperature range of from 20 to 80° C., with the optimum temperature being 50 to 60° C.

5) Temperature Stability

It exhibits residual activity not less than 80% at 40° C. when treated for 30 minutes in a 50 mM glycine sodium hydroxide buffer (pH 10), while it exhibits residual activity of about 60% even at 45° C.

In addition, the invention enzymes having the below-described properties 6) are more preferred.

6) Oxidizing-agent-resisting Performance

It exhibits residual activity not less than 70% after treated at pH 10 and 30° C. for 60 minutes in the presence of 2% $H_2O_2$.

Although there is no particular limitation imposed on the specific activity of the invention enzyme, that having specific activity as described below in 7) is particularly preferred.

7) Specific Activity

The specific activity calculated from the enzyme activity of it when reacted at pH 10 and 50° C. for 15 minutes (with a soluble starch as a substrate) and a protein concentration as measured by a protein assay kit (product of Bio-rad Laboratories) is 3000 U/mg or greater.

Examples of the invention enzyme include those having an amino acid sequence as shown in the Sequence Listing (SEQ ID NOS:2 or 4) to be described subsequently herein and those having the above-described amino acid sequence except for having in a part thereof substitution, deletion or addition of one or more than one amino acids. Concerning the substitution, deletion or addition, homology of at least 80% is preferred, with that of at least 90% being particularly preferred. Incidentally, the homology is calculated by the Lipman-Pearson method (Science, 227, 1435(1985)).

One of the characteristics of the amino acid sequence of the invention enzyme is that different from the liquefying α-amylases known to date which have markedly highly conserved 13 amino acid residues at a calcium linkage site, the invention enzyme has a low conservation ratio. Particularly, five residues, among eight residues which correspond to aspartic acid having a carboxyl side chain playing an important role in binding of calcium atoms in the conventional liquefying α-amylase, are asparagine or serine without carboxyl-side chain in the invention enzyme, which suggests that no calcium is contained in the molecule. In other words, the invention enzyme is presumed to have high chelating-agent-resisting performance because it does not need calcium for the expression of enzyme activity. As such a liquefying α-amylase having a low conservation ratio of amino acid residues at the calcium linkage site and therefore being not so dependent on calcium, only that derived from Pyrococcus sp. is known [Appl. Environm. Microbiol., 63, 3569(1997)]. This enzyme however is not suited for use as a component for a detergent, because it is an acidic amylase having the optimum acting pH at around 5.5 to 6 and its activity largely lowers at a temperature not greater than 50° C. The homology of the amino acid sequence of this enzyme with that of the invention enzyme is only about 30%, indicating that the liquefying alkaline α-amylase of the present invention is utterly different from this enzyme. Accordingly, the liquefying alkaline α-amylase according to the present invention is a novel enzyme which can be strictly distinguished from the liquefying α-amylases known to date.

The enzyme of the present invention is prepared, for example, by culturing target-enzyme-producing bacteria belonging to Bacillus sp. and collecting the enzyme from the culture. Examples of such target-enzyme-producing bacteria include the strains KSM-K36 and KSM-K38 each having the below-described mycological properties.

TABLE I

|   | Strain KSM-K36 | Stain KSM-K38 |
|---|---|---|
| (a) Results of microscopic observation | The strains K36 and K38 are bacilli having a size of 1.0 to 1.2 μm × 2.4 to 5.4 μm and 1.0 to 1.2 μm × 1.8 to 3.8 μm, respectively. They form an oval endospore (1.0 to 1.2 μm × 1.2 to 1.4 micron) at the center or near the end of the cell. Positive in the Gram's stain. Having no acid resistance. | |
| (b) Growth in various media Since the present strain is alkaliphilic, 0.5% sodium carbonate is added to the medium employed in the following tests. | | |
| Nutrient agar plate culture | Good growth is observed. The colony has a circular shape. It has a flat surface, but a rough periphery. The color of the colony is pale earthlike color. | Good growth is observed. The colony has a circular shape. It has a flat surface and a smooth periphery. The color of the colony is yellowish brown. |

TABLE I-continued

| | Strain KSM-K36 | Stain KSM-K38 |
|---|---|---|
| Nutrient agar slant culture | Growth is observed. | Growth is observed. |
| Nutrient broth cutture | Growth is observed. | Growth is observed. |
| Nutrient-gelatin stab culture | Good growth is observed. No liquefaction of gelatin is observed. | Good growth is observed. No liquefaction of gelatin is observed. |
| Litmus milk | No change is observed. | No change is observed. |
| (c) Physiological properties | | |
| Reduction of a nitrate and denitrification reaction | Reduction of a nitrate is positive. Denitrification reaction is negative. | Reduction of a nitrate is positive. Denitrification reaction is negative. |
| MR test | Owing to the alkaline medium, judgment is impossible. | Owing to the alkaline medium, judgment is impossible. |
| V-P test | Negative. | Negative. |
| Formation of indole | Negative. | Negative. |
| Formation of hydrogen nitride | Negative. | Negative. |
| Hydrolysis of starch | Positive. | Positive. |
| Assimilation of citric acid | It grows on a Christensen's medium, but not on a Koser's medium and Simmon's medium. | It grows on a Christensen's medium, but not on a Koser's medium and Simmon's medium. |
| Assimilation of an inorganic nitrogen source | It assimilates a nitrate but not an ammonium salt. | It assimiiates a nitrate but not an ammonium salt. |
| Formation of a colorant | Formation of a pale yellow colorant on King's B medium. | Negative. |
| Urease | Negative. | Negative. |
| Oxidase | Negative. | Negative. |
| Catalase | Positive. | Positive. |
| Range for growth | Temperature range for growt is 15 to 40° C. The optimum growth temperature ranges from 30 to 37° C. The pH range for growth is 8.0 to 11.0. The optimum growth pH is pH 10.0 to 11.0. | Temperature range for growth is 15 to 40° C. The optimum growth temperature is 30° C. The pH range for growth is 9.0 to 11.0. The optimum growth pH is similar to the above. |
| Behavior to oxygen | Aerophilic. | Aerophilic. |
| O-F test | No growth is observed. | No growth is observed. |
| Assimilation of saccharides | Assimilated are D-galactose, D-xylose, L-arabinose, lactose, glycerin, meribiose, libose, D-glucose, D-mannose, maltose, sucrose, trehalose, D-mannitol, starch, raffinose and D-fructose. | |
| Growth on a salt-containing medium | Grown at a salt concentration of 12%, but no growth at a salt concentration of 15%. | |

As a result of investigation based on the above-described microbiological properties while making reference to "Bergey's Manual of Systematic Bacteriology" [Williams & Wilkins, United States of America (1986)] and "The Genus Bacillus" [Agricultural Research Service, Washington, D.C. (1973)], these cell strains are recognized to be endospore-producing bacillus belonging to Bacillus sp. Since they cannot grow in the neutral range but exhibit good growth in the high alkaline range, they belong to alkaliphilic microorganisms and can be distinguished from the conventional bacteria belonging to Bacillus sp. which show growth in the neutral range. In addition, microbiological and physiological properties of them were compared with those of known alkaliphilic bacilli [Microbiol., 141, 1745(1995)]. As a result, neither the strain KSM-K36 nor the strain KSM-K38 agrees with any known alkaliphilic bacillus. Each of the strains KSM-K36 and KSM-K38 was therefore judged as a novel strain and was deposited under the name of FERM BP-6945 and FERM BP-6946 with National Institute of Bioscience and Human-Technology, Agency of Industrial Science and Technology, Ministry of Industrial Trade and Technology.

The liquefying alkaline amylase according to the present invention can be obtained by inoculating the above-described microorganism to a medium, followed by incubation in a conventional manner. Since the microorganism is alkaliphilic, the alkaline medium is preferred. The target liquefying alkaline amylase can be collected from the thus obtained culture. The supernatant can be used as is. Alternatively, it can be used as a purified enzyme after subjecting it to salting-out, precipitation or ultrafiltration to obtain a crude enzyme as needed and then, purifying and crystallizing in a conventional manner.

One example of the purification process of the liquefying alkaline amylase of the present invention will next be mentioned. By subjecting the culture supernatant to (1) ammonium sulfate precipitation, (2) DEAE-Toyopearl (TOSOH Corporation) column chromatography or (3) gel filtration, it is possible to obtain a purified enzyme which provides a single band in polyacrylamide electrophoresis (gel concentration 10%) and sodium dodecyl sulfate (SDS) electrophoresis.

The liquefying alkaline amylase according to the present invention can also be prepared by obtaining a gene encoding the liquefying alkaline amylase of the present invention and a vector plasmid containing it, transforming a suitable microorganism, preferably a bacterium belonging to Bacillus sp. by using the plasmid and then incubating the transformed microorganism or bacterium.

Examples of the gene encoding the liquefying alkaline amylase of the present invention include those having a nucleotide sequence as shown in the Sequence Listing (SEQ ID NOS:1 and 3) to be described subsequently herein.

As described above, the liquefying alkaline amylase according to the present invention has the optimum pH on the alkaline side and has high chelating-agent-resisting performance so that it is particularly useful as an enzyme to be incorporated in a detergent. The liquefying alkaline amylase of the present invention has strong oxidizing-agent-resistance as described above so that it can added to a detergent having an oxidizing agent such as bleaching agent incorporated therein. The amount of the invention enzyme to a detergent is preferably 0.001 to 5 wt. %.

In addition to the above-described liquefying alkaline amylase, known detergent components can be added to the detergent composition of the present invention. Examples of the known detergent component include those described in page 5, upper right column, line 14 to the same page, lower right column, line 29 of WO94/26881, for example, surfactant, chelating agent, alkaline agent, inorganic salt, bleaching agent and fluorescent agent.

A surfactant is added in an amount of 0.5 to 60 wt. %. (which will hereinafter be indicated "%", simply) in a detergent composition, more specifically, 10 to 45% in a powdery detergent composition and 20 to 50% in a liquid detergent composition. When the detergent composition of the present invention is a bleaching detergent or automatic dish washing detergent, a surfactant is generally added in an amount of 1 to 10%, preferably 1 to 5%, a divalent metal ion scavenger is added in an amount of 0.01 to 50%, preferably 5 to 40% and an alkali agent and an inorganic salt are added in a total amount of 0.01 to 80%, preferably 1 to 40%.

A recontamination preventive is added in an amount of 0.001 to 10%, preferably 1 to 5%.

In addition to the amylase of the present invention, protease, cellulase, protopectinase, pectinase, lipase, hemicellulase, β-glycosidase, glucose oxidase, cholesterol oxidase and the like can be employed. These enzymes can be added in an amount of 0.001 to 5%, preferably 0.1 to 3%. The bleaching agent (ex. hydrogen peroxide, percarbonate or the like) is preferably added in an amount of 1 to 10%. Upon use of the bleaching agent, a bleaching activator can be added in an amount of 0.01 to 10%. Examples of the fluorescent agent include biphenyl type fluorescent agents (ex. "Chinopearl CBS-X", trade name) and stilbene type fluorescent agents (ex. DM type fluorescent dye). It is preferred to add the fluorescent agent in an amount of 0.001 to 2%.

The above-described detergent composition can be provided in the form of liquid, powder, granule or the like. This detergent composition can be used as a laundry detergent, automatic dish washing detergent, pipe detergent, artificial tooth detergent or bleaching agent.

EXAMPLES

The enzyme activity was measured in accordance with the below-described method by using the following buffers:

| pH 4.5 to 6.0 | acetate buffer |
| pH 6.0 to 8.0 | potassium phosphate buffer |
| pH 9.0 to 10.5 | glycine sodium hydroxide buffer |
| pH 10.0 to 12.0 | carbonate buffer |
| pH 4.0 to 12.0 | Britton-Robinson buffer |

Measuring Method of the Activity of Amylase

1. Preparation Process of a Reagent (Preparation of a 1% aqueous solution of soluble starch)

In 400 mL of deionized water was suspended 5 g of soluble starch (potato-derived starch, product of Sigma Chemical Co., Ltd.). While stirring in a boiling water, the suspension was dissolved by heating for about 10 minutes, followed by the addition of deionized water to give a total volume of 500 mL.

(Preparation of a 250 mM Glycine Sodium Hydroxide Buffer (pH 10))

In about 300 mL of deionized water was dissolved 9.38 g of glycine (guaranteed class, product of Wako Pure Chemical Industries, Ltd.), followed by adjustment of the resulting solution to pH 10 with an about 5N aqueous sodium hydroxide solution by using a pH meter. To the pH-adjusted solution was added deionized water to give a total volume of 500 mL.

(Preparation of a DNS Reagent)

In 300 mL of deionized water was dissolved 8 g of sodium hydroxide (guaranteed class, product of Wako Pure Chemical Industries, Ltd.). To the resulting solution was added 2.5 g of 3,5-dinitrosalicylic acid (DNS, guaranteed class, product of Wako Pure Chemical Industries, Ltd.) in portions, while dissolving the latter in the former. After DNS was completely dissolved, 150 g of sodium potassium tartrate (guaranteed class, product of Wako Pure Chemical Industries, Ltd.) was added. After complete dissolution, deionized water was added to the resulting solution to give a total volume of 500 mL.

(Preparation of a Glucose Solution for a Calibration Curve)

Using a glucose standard solution (for photoelectric use, product of Wako Pure Chemical Industries, Ltd.) and deionized water, glucose solutions of 0, 1, 2, 3, 4 and 5 μmol/0.1 ml were prepared, respectively.

2. Measuring Method of the Activity of Amylase (Dilution of an Enzyme Solution)

The purified enzyme was diluted with a 10 mM glycine sodium hydroxide buffer (pH 10) to give a δ-absorbance [=(absorbance of a sample)—(absorbance of a blank)] not greater than 0.6.

(Measurement of a Sample)

In a test tube, 0.5 mL of the 1% aqueous solution of soluble starch, 0.2 mL of the 250 mM glycine sodium hydroxide buffer (pH 10) and 0.2 mL of deionized water (said mixture will hereinafter be called "substrate solution") were charged, followed by preliminary heating for about 5 minutes in a water bath of 50° C. After preliminary heating, 0.1 ml of a properly diluted enzyme solution was added to the reaction mixture, followed by reaction at 50° C. for 15 minutes. After completion of the reaction, 1.0 mL of the DNS reagent was added to the reaction mixture, followed by color development by heating in boiling water for 5 minutes. Immediately after that, the solution was allowed to cool down in an ice-water bath. The resulting solution, after cooling, was added with 4.0 mL of deionized water, followed by mixing. The absorbance of the solution at 535 nm was then measured.

(Measurement of Blank)

In a test tube, 0.9 mL of the substrate solution was charged, followed by the addition of 1.0 mL of the DNS reagent and then with 0.1 mL of an enzyme solution. The resulting mixture was heated in a boiling water for 5 minutes to cause color development. Immediately after that, the reaction mixture was allowed to cool down in ice water. After cooling, 4.0 mL of deionized water was added to the reaction mixture, followed by mixing. The absorbance of the solution at 535 nm was then measured.

(Preparation of a Calibration Curve)

In a test tube, 0.9 mL of the substrate solution was charged, followed by the addition of 1.0 mL of the DNS reagent and then with 0.1 mL of each of the glucose solutions for a calibration curve having various concentrations. The resulting mixture was heated in boiling water for 5 minutes to cause color development. Immediately after that, the solution was allowed to cool down in ice water. The resulting solution, after cooling, was added with 4.0 mL of deionized water, followed by mixing. The absorbance of the solution at 535 nm was then measured. On a graph, the glucose concentration ($\mu$mol/0.1 mL) was plotted as abscissa and the absorbance as ordinate and the slope of those linear plots was determined by the least square method. A conversion factor (F) was calculated in accordance with the following formula:

$$\text{Conversion Factor }(F)=[1/(\text{slope})]\times[1/15]\times[1000/0.1]$$

Incidentally, a calibration curve was prepared whenever activity was measured.

(Calculation of Activity)

With the amount of the enzyme which formed reducing sugar equivalent to 1 $\mu$mol of glucose in one minute was defined as one unit (1U), the titer of the enzyme was calculated in accordance with the following formula:

$$\text{Activity of Amylase }(U/L)=[\delta\text{-absorbance}]\times[\text{conversion factor }(F)]\times[\text{dilution ratio}]$$

[Testing Method of Chelating-agent-resisting Performance]

(Preparation of an EDTA Solution)

After 9.3 g of EDTA (product of Sigma Chemical Co., Ltd.) was dissolved in about 80 mL of deionized water, the resulting solution was adjusted to pH 8 with an about 5N aqueous sodium hydroxide solution by using a pH meter. To the pH-adjusted solution, deionized water was added to give a total volume of 100 mL, whereby a 250 mM EDTA solution was prepared. The resulting solution was diluted with deionized water to prepare 10 to 100 mM EDTA solutions.

After 9.5 g of EGTA (product of Sigma Chemical Co., Ltd.) was dissolved in about 80 mL of deionized water, the resulting solution was adjusted to pH 8 with an about 5N aqueous sodium hydroxide solution by using a pH meter. To the pH-adjusted solution, deionized water was added to give a total volume of 100 mL, whereby a 250 mM EGTA solution was prepared. The resulting solution was diluted with deionized water to prepare 10 to 100 mM EGTA solutions.

(Testing Method of Chelating-agent-resisting Performance)
In the Case of Treatment with 1 mM EDTA at 45° C. for 30 Minutes In a test tube, 0.1 mL of the 10 mM EDTA solution, 0.2 mL of the 250 mM glycine sodium hydroxide buffer (pH 10) and 0.1 mL of deionized water were charged, followed by preliminary heating in a water bath of 45° C. for about 5 minutes. After preliminary heating, 0.1 mL of an enzyme solution diluted properly with a 10 mM glycine sodium hydroxide buffer (pH 10) was added to the reaction mixture. The resulting mixture was kept at a temperature of 45° C. for 30 minutes. Thirty minutes later, a 0.1 mL portion of the resulting solution was added to 0.9 mL of the substrate solution preliminary heated in a water bath of 50° C. and the residual enzyme activity was measured in accordance with the amylase activity measuring method.

[Testing Method of Oxidizing-agent Resisting Performance]

In a test tube, 0.067 mL of hydrogen peroxide (a 30% aqueous hydrogen peroxide solution, product of Wako Pure Chemical Industries, Ltd.), 0.2 mL of the 250 mM glycine sodium hydroxide buffer (pH 10) and 0.633 mL of deionized water were charged, followed by preliminary heating in a water bath of 30° C. for about 5 minutes. After preliminary heating, 0.1 mL of an enzyme solution properly diluted with a 10 mM glycine sodium hydroxide buffer (pH 10) was added to the reaction mixture. The resulting mixture was kept at 30° C. for 60 minutes. Sixty minutes later, a 0.2 mL portion of the resulting solution was charged in a test tube containing 1 $\mu$L of catalase (derived from bovine liver, product of Boehringer Mannheim GmbH) placed in advance in ice water, whereby hydrogen peroxide was deactivated and the reaction was terminated. Then, a 0.1 ml portion of the reaction-terminated solution was added to 0.9 mL of the substrate solution preliminary heated in a water bath of 50° C. and residual enzyme activity was measured in accordance with the amylase activity measuring method.

[Quantitative Analysis of Protein]

Quantitative analysis of a protein was carried out in accordance with the standard assay method by Protein Assay Kit II (catalogue No. 500-0002, product of Bio-rad Laboratories) with bovine serum albumin attached to the kit as a standard protein.

Example 1

Screening of Liquefying Alkaline Amylases Having Chelating-agent-resisting Performance In sterilized water was suspended about 0.5 g of soil, followed by heating at 80° C. for 15 minutes. The supernatant after heat treatment was diluted properly with sterilized water, and then it was spread onto an agar medium A for isolation of amylase-producing microorganisms. Colonies were then formed by incubation at 30° C. for 2 days. The colony having at the periphery thereof a transparent halo formed by the hydrolysis of starch was selected and it was separated as amylase-producing bacteria. The isolated bacteria were inoculated on a medium B, followed by aerobic culture at 30° C. for 2 days under shaking. After centrifugal separation of the resulting culture, chelating-agent (EDTA) resisting performance of crude amylase in the resulting supernatant was measured. In addition, the optimum pH of the crude amylase was measured, and thus bacteria producing the liquefying alkaline amylase of the present invention were screened.

According to the above-described method, the strain KSM-K36 and the strain KSM-K38 each belonging to the Bacillus sp. were obtained.

| Medium A: | Tryptone | 1.5% |
|---|---|---|
| | Soytone | 0.5% |
| | Sodium chloride | 0.5% |
| | Colored starch | 0.5% |

-continued

|  | Agar | 1.5% |
|---|---|---|
|  | Na$_2$CO$_3$ | 0.5% |
|  | (pH 10) |  |
| Medium B: | Tryptone | 1.5% |
|  | Soytone | 0.5% |
|  | Sodium chloride | 0.5% |
|  | Soluble starch | 1.0% |
|  | Na$_2$CO$_3$ | 0.5% |
|  | (pH 10) |  |

Example 2

Culture of the Strains KSM-K36 and KSM-K38

On the liquid medium B as described in Example 1, each of the strains KSM-K36 and KSM-K38 was inoculated, followed by aerobic culture at 30° C. for 2 days under shaking. The amylase activity (pH 8.5) of the supernatant obtained by centrifugal separation was measured. As a result, it has been found that the culture solutions had activity of 1177 U and 557 U/L, respectively.

Example 3

Purification of the Liquefying Alkaline Amylases of the Present Invention

Ammonium sulfate was added to the supernatant culture of the strain Bacillus sp. KSM-K36 to give 80% saturation, followed by stirring. The precipitate so formed was collected and dissolved in a 10 mM Tris-hydrochloric acid buffer (pH 7.5) containing 2 mM CaCl$_2$, followed by dialysis overnight against the buffer. The inner dialyzate was thereafter applied to DEAE-TOYOPEARL 650 M column which had been equilibrated with the same buffer, and then protein was eluted with a linear concentration gradient of NaCl (0 M to 1 M) in the same buffer. After dialysis of active fractions against the above-described buffer, further purification was carried out by gel-filtration column chromatography. Active fractions thus obtained were dialyzed against the same buffer, which made it possible to obtain a purified enzyme providing a single band by both polyacrylamide gel electrophoresis (gel concentration: 10%) and sodium-dodecylsulfate (SDS) polyacrylamide gel electrophoresis. From the supernatant culture of the strain Bacillus sp. KSM-K38, another purified enzyme was obtained by the similar method.

Example 4

Chelating-agent-resisting Performance of the Liquefying Alkaline Amylases of the Present Invention Using two purified liquefying alkaline amylases (which will hereinafter be abbreviated as "K36" and "K38", respectively) of the present invention obtained respectively from the strains KSM-K36 and KSM-K38 in Example 3, resisting performance against various chelating agents was measured.

1) EDTA or EGTA Resisting Performance

To a 50 mM glycine sodium hydroxide buffer (pH 10) containing EDTA or EGTA (each, product of Sigma Co., Ltd.) having a final concentration of 0 to 100 mM, a purified enzyme properly diluted with a 10 mM glycine sodium hydroxide buffer (pH 10), followed by treatment at a predetermined temperature (30° C., 40° C. or 45° C.) for 30 minutes. The residual enzyme activity of the reaction mixture was measured in accordance with the amylase activity measuring method [with a 50 mM glycine sodium hydroxide buffer (pH 10)]. As a control, purified products of Termamyl and Duramyl (each, purified from products of Novo Industry A/S in the granular form), which were amylases derived from Bacillus licheniformis, were employed.

Figure 2:
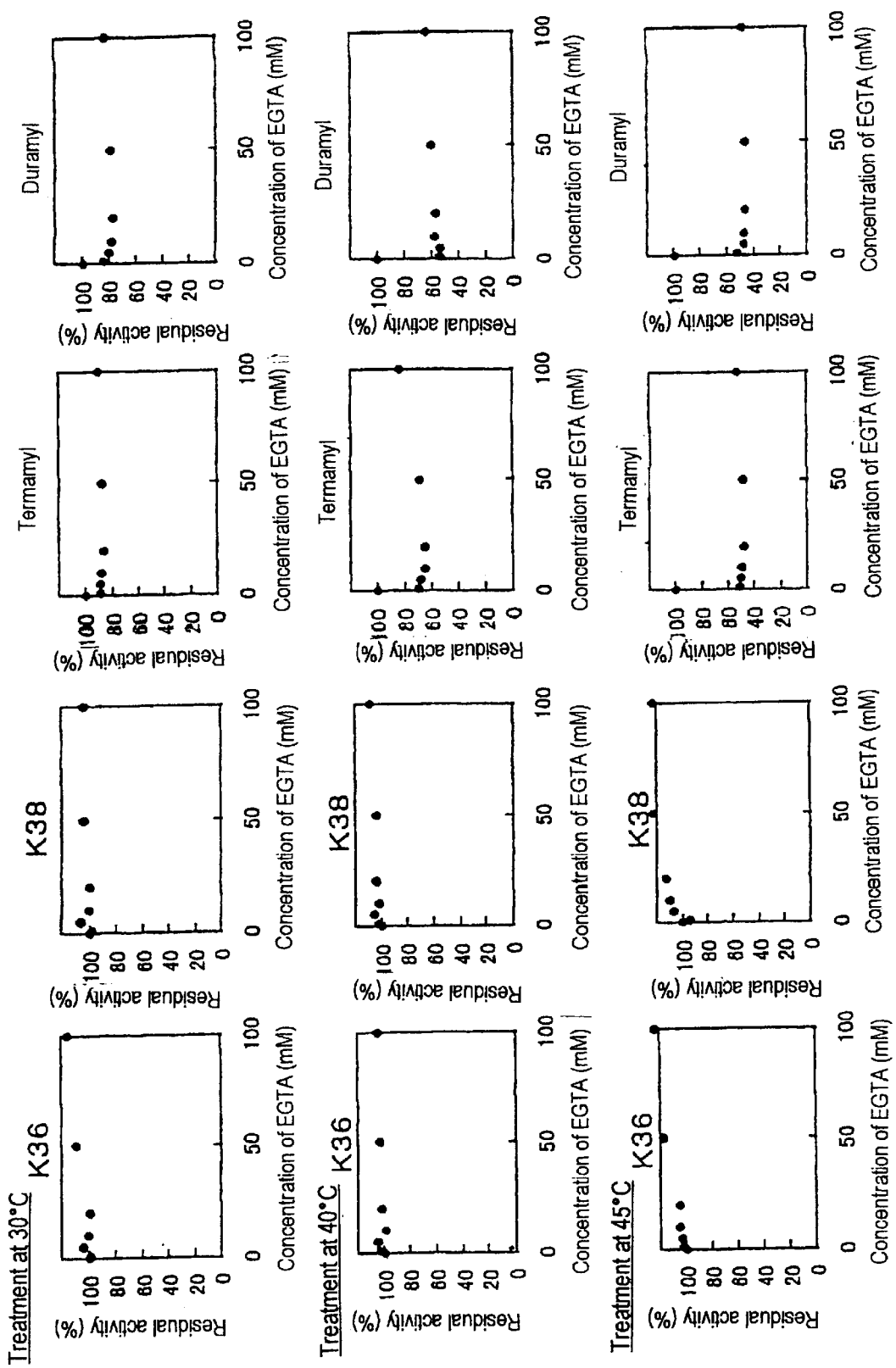
FIG. 2 is a diagram illustrating a relationship between a treating concentration with EGTA and residual activity, of each of the liquefying alkaline amylases (K36 and K38) according to the present invention and known amylases used for a detergent.
Figure 3:
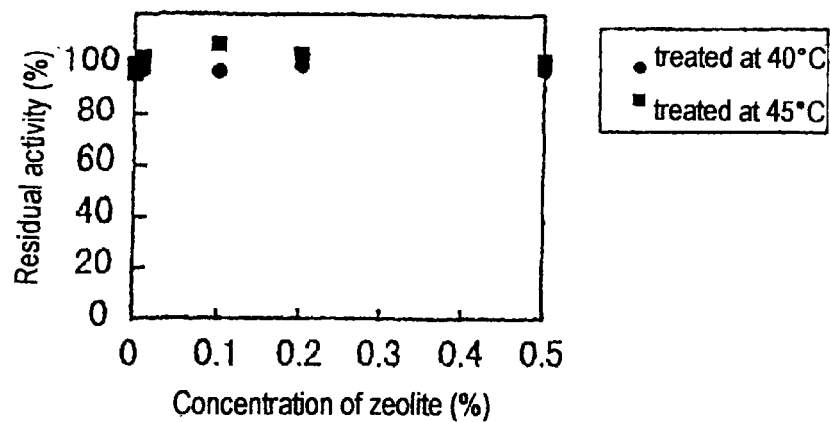
FIG. 3 is a diagram illustrating a relationship between a treating concentration with zeolite and residual activity, of the liquefying alkaline amylase K36 according to the present invention.
Figure 4:
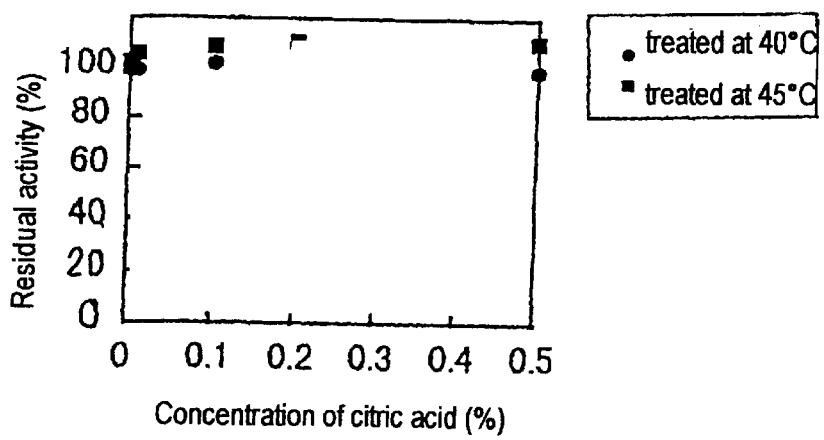
FIG. 4 is a diagram illustrating a relationship between a treating concentration with citric acid and residual activity, of the liquefying alkaline amylase K36 according to the present invention.
Figure 5:
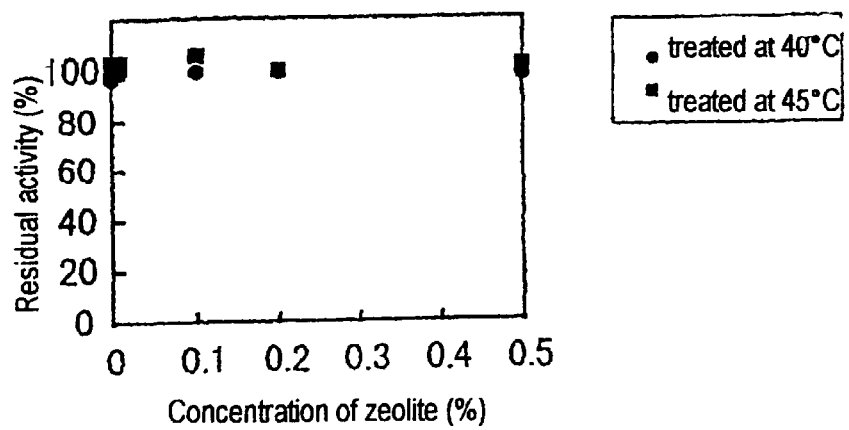
FIG. 5 is a diagram illustrating a relationship between a treating concentration with zeolite and residual activity, of the liquefying alkaline amylase K38 according to the present invention.
Figure 6:
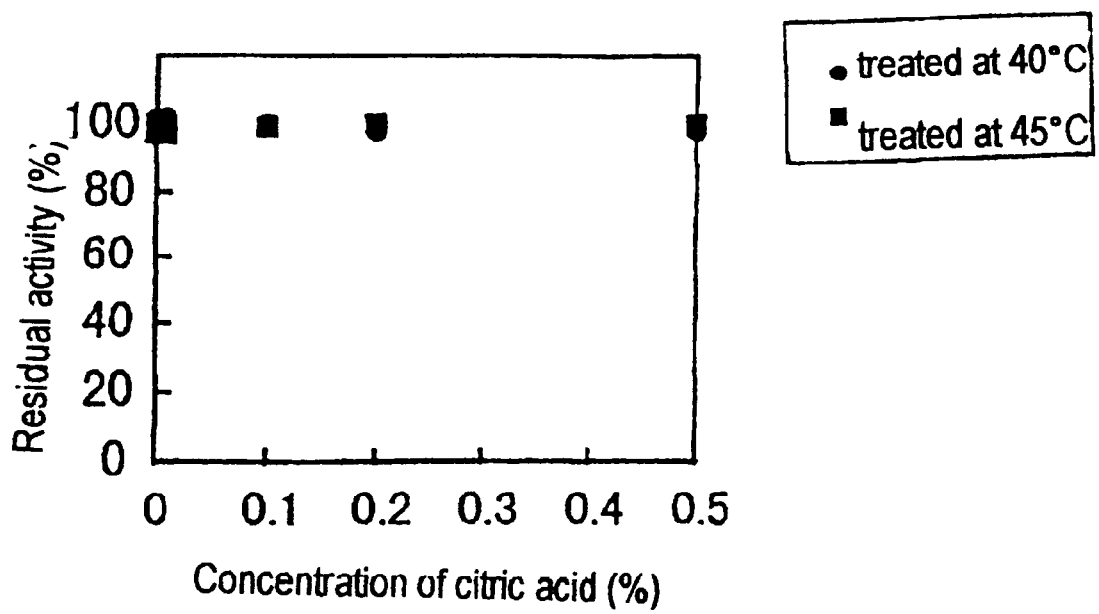
FIG. 6 is a diagram illustrating a relationship between a treating concentration with citric acid and residual activity, of the liquefying alkaline amylase K38according to the present invention.

As illustrated in FIGS. 1 and 2, it was confirmed that K36 and K38 each had high resisting performance compared with Tarmamyl and Duramyl, not influenced by highly concentrated EDTA or EGTA.

2) Resisting Performance Against Citric Acid or Zeolite

To a 50 mM glycine sodium hydroxide buffer (pH 10) containing trisodium citrate dihydrate (guaranteed class product of Wako Pure Chemical Industries, Ltd.) or synthetic zeolite A-3 (product of Wako Pure Chemical Industries, Ltd.) having each of final concentrations of 0 to 0.5%, a purified enzyme properly diluted with a 10 mM glycine sodium hydroxide buffer (pH 10) was added, followed by treatment at each of predetermined temperatures (40° C. and 45° C.) for 30 minutes. The residual enzyme activity of the reaction mixture was measured in accordance with the amylase activity measuring method [with a 50 mM glycine sodium hydroxide buffer (pH 10)].

As a result, it was confirmed that each of K36 and K38 was influenced by neither citric acid nor zeolite (as illustrated in FIGS. 3 to 6).

Example 5

Acting pH and Optimum Acting pH of the Liquefying Alkaline Amylases of the Present Invention The acting pH and optimum acting pH of each of K36 and K38 were measured in accordance with the amylase activity measuring method by using various buffers having a final concentration of 50 mM [acetate buffer (pH 4.5 to 6.0), potassium phosphate buffer (pH 6.0 to 8.0), glycine sodium hydroxide buffer (pH 9.0 to 10.5) and carbonate buffer (pH 10.0 to 12.0)] and they were indicated by relative activity with the maximum activity as 100%.

Figure 7:
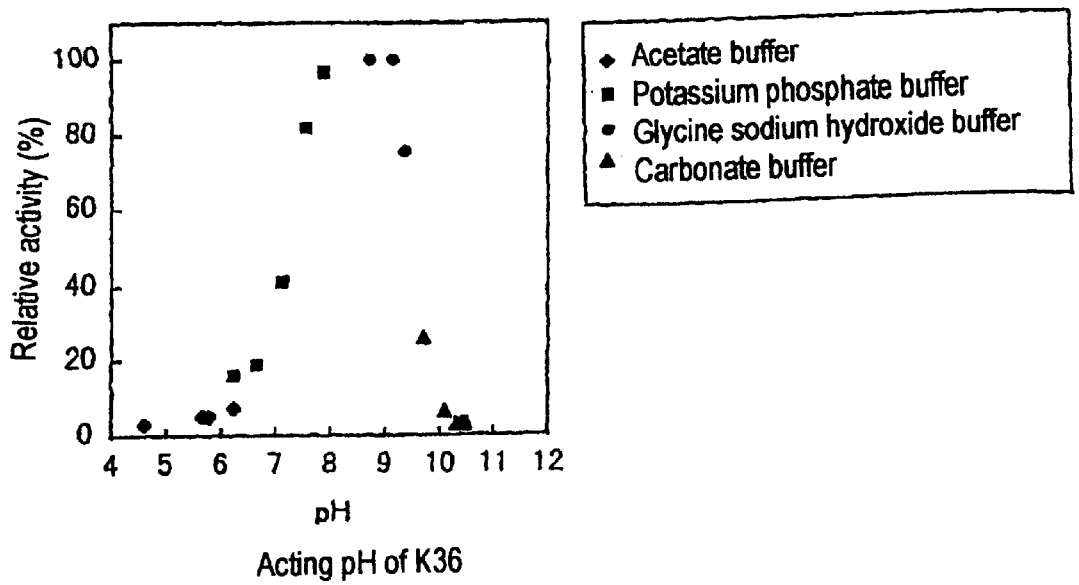
FIG. 7 is a diagram illustrating a relationship between a reaction pH and relative activity, of the liquefying alkaline amylase K36 according to the present invention.
Figure 8:
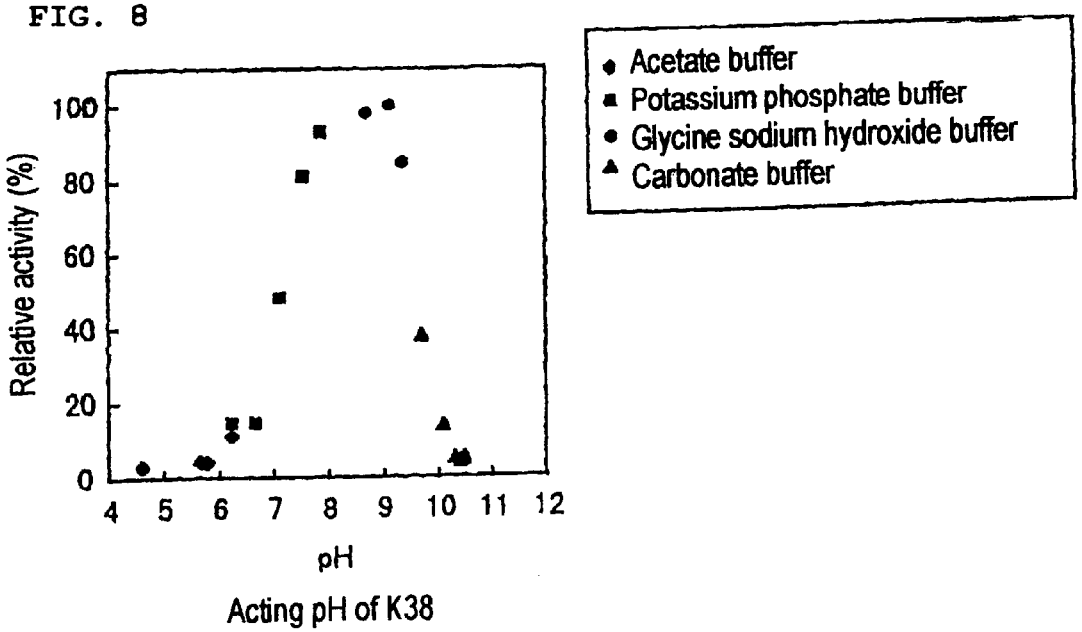
FIG. 8 is a diagram illustrating a relationship between a reaction pH and relative activity, of the liquefying alkaline amylase K38 according to the present invention.

As a result (as illustrated in FIGS. 7 and 8), it was confirmed that each of K36 and K38 acted within a pH range of 6.0 to 10.0 and the optimum acting pH was 8.0 to 9.0. Incidentally, the pH indicated was the actually measured value of the reaction mixture.

Example 6

Oxidizing-agent-resisting Performance and Relative Enzyme Activity of the Liquefying Alkaline Amylases of the Present Invention An enzyme (K36, K38, Tarmamyl or Duramyl) properly diluted with a 10 mM glycine sodium hydroxide buffer (pH 10) was added to a 50 mM glycine sodium hydroxide buffer (pH 10) containing H$_2$O$_2$ having a final concentration of 2% (580 mM), followed by treatment at 30° C. for 60 minutes. The residual activity was measured at appropriate intervals in accordance with the amylase activity measuring method [with a 50 mM qlycine sodium hydroxide buffer (pH 10)]. The oxidizing-agent-resisting performance was indicated by residual activity with activity before treatment as 100%.

As a result (FIG. 9), it was recognized that each of K36 and K38 maintained the residual activity not less than 70%, particularly not less than 94%, even after treatment at pH 10 and 30° C. for 60 minutes in the presence of 2% H$_2$O$_2$ and thus had sufficient oxidizing-agent-resisting performance.

The specific activities of K36 and K38 calculated from the value of enzyme activity when reacted at pH 10 and 50° C. for 15 minutes (with a soluble starch as a substrate) and the concentration of protein as measured by a protein assay kit (product of Bio-rad Laboratories) were 4300 U/mg and 3600 U/mg, respectively (Table 2). It revealed that each enzyme has a specific activity not less than 3000 U/mg, markedly high specific activity compared with oxidizing-agent-resistant enzymes (LAMY·M202T (WO98/44126) and Duramyl) formed by protein engineering. Accordingly, the liquefying alkaline amylases of the present invention are advantageous from the viewpoints of an amount to be added to a detergent, industrial fermentation production and the like.

TABLE 2

Comparison of specific activity

| Enzyme | Specific activity (U/mg) |
|---|---|
| K36 | 4300 |
| K38 | 3600 |
| LAMY* | 4000 |
| LAMY·M202T** | 1700 |
| Duramyl | 500 |

*LAMY: derived from the strain Bacillu3 sp. KSM-1378.
**LAMY·M202T: the above enzyme substituted with Met202Thr.

Enzyme activity: activity when reacted at 50° C. for 15 minutes (with a soluble starch as a substrate) by using a glycine sodium hydroxide buffer (pH 10).
Amount of protein: measured by a protein assay kit (product of Bio-rad Laboratories)

Example 7

Other Enzymatic Properties of the Liquefying Alkaline Amylases (K36 and K38) of the Present Invention These two purified enzymes were analyzed to have the following properties:
(1) Action
Each of them hydrolyses α-1,4-glucosidic linkages in starches, amylose, amylopectin and partial degradation products thereof and from amylose, forms glucose (G1), maltose (G2), maltotriose (G3), maltotetraose (G4), maltopentaose (G5), maltohexaose (G6) and maltoheptaose (G7). It however does not act on pullulan.
(2) pH Stability (Britton-Robinson Buffer)
Each of them exhibits residual activity not less than 70%, when treated at 40° C. for 30 minutes within a pH range of from 6.5 to 11.0.
(3) Acting Temperature Range and Optimum Acting Temperature
Each of them acts in a wide temperature range of from 20° C. to 80° C., with the optimum acting temperature being 50 to 60° C.
(4) Temperature Stability
As a result of treatment in a 50 mM glycine sodium hydroxide buffer (pH 10) at varied temperatures for 30 minutes to study conditions of deactivation, each of them exhibited residual activity not less than 80% at 40° C. and even about 60% at 45° C.
(5) Molecular Weight
Each of them has a molecular weight of 55,000±5,000 as measured in accordance with the sodium dodecyl sulfate polyacrylamide gel electrophoresis.
(6) Isoelectric Point
Each of them has an isoelectric point of around pH 4.2 when measured by isoelectric focusing electrophoresis.
(7) Effects of Surfactants
Each of them is substantially free from activity inhibition (activity remaining ratio not less than 90%) when treated at pH 10 and 30° C. for 30 minutes in a 0.1% solution of a surfactant such as sodium linear alkylbenzene sulfonates, sodium alkylsulfate esters, sodium polyoxyethylene alkylsulfate esters, sodium α-olefinsulfonates, sodium α-sulfonated fatty acid esters, sodium alkylsulfonates, DSD, soaps or softanol.
(8) Effects of Metal Salts
Each of them was treated at pH 10 and 30° C. for 30 minutes in the presence of various metal salts, whereby their effects were studied. As a result, K36 is inhibited by 1 mM of $Mn^{2+}$ (inhibition ratio: about 95%) and slightly inhibited by 1 mM of $Hg^{2+}$, $Be^{2+}$ or $Cd^{2+}$ (inhibition ratio: 30 to 40%). K38 is inhibited by 1 mM of $Mn^{2+}$ (inhibition ratio: about 75%) and slightly inhibited by 1 mM of $Sr^{2+}$ or $Cd^{2+}$ (inhibition ratio: about 30%).
(9) N-terminal Amino Acid Sequence
The N-terminal amino acid sequence of each of the present amylases was determined by Edman degradation [Edman, P., Acta Chem. Scand., 4 , 283 (1948)] with a protein sequencer (model 477A manufactured by ABI Corp.). As a result, it was found to have a sequence of Asp-Gly-Leu-Asn-Gly-Thr-Met-Met-Gln-Tyr-Tyr-Glu-Trp-His-Leu (SEQ ID NO:5).

Example 8

Evaluation of Detergency of an Automatic Dish Washing Detergent Containing Each of the Present Liquefying Alkaline Amylases Detergency of an automatic dish washing detergent containing each of the present liquefying alkaline amylases (K36 and K38) was evaluated under the below-described conditions. As a control, a detergent free from the invention enzyme was used.
1) Preparation of Soiled Dishes
To a porcelain dish was applied 1 mL of oatmeal (Quaker Corp.) which had been boiled in boiling tap water and then added with tap water to dissolve therein. After the dish was dried at room temperature for 3 hours, it was stored at 5° C. (semi-hermetically-sealed condition) until provided for use. Three dishes were prepared in this way for washing once.
2) Washing Conditions
Washer employed: Full automatic dish washer "NP-810", trade name; manufactured by Matsushita Electric Industries Co., Ltd.
Washing temperature: Water temperature is increased gradually to about 55° C.
Water used for washing: tap water
Concentration of the detergent: 0.2 wt. %
Washing time: washing for about 20 minutes→rinsing for about 20 minutes (standard course)
Amount of water circulated upon washing: 3.5 L.
3) Composition of the detergent (% indicates wt. %)
2.2% of "Pullulonic L-61", 24.7% of sodium carbonate, 24.7% of sodium bicarbonate, 10.0% of sodium percarbonate, 12.0% of No.1 sodium silicate, 20.0% of trisodium citrate, 2.2% of "Propylene glycol 3000", 0.2% of silicone "KST-04" (trade name; product of Toshiba Silicone Co., Ltd.) and 4.0% of socaran "CP-45" (trade name; product of BASF AG)

4) Amount of the Enzyme to be Added

The activity value of each of the purified enzymes which had been obtained in Example 3 was measured by the above-described amylase activity measuring method by using as a buffer a glycine-sodium hydroxide buffer (pH 10). Based on the result, the amylase was added to the detergent in an amount of 150 U.

5) Evaluation Method of Detergency

An iodine solution was applied to the dish after washing and the color due to iodo-starch reaction was macroscopically judged.

As a result, the detergent containing each of the present enzymes removed the stain completely, thus exhibiting excellent detergency compared with the detergent free from the present enzyme.

Example 9

With the DNA of the chromosome of each of the strains KSM-K36 and KSM-K38 extracted by the Saito-Miura method [Biochim. Biophys. Acta, 72, 619(1961)] as a template, PCR was effected in a conventional manner by using two oligonucleotide primers which had been designed based on the sequences Met-Gln-Tyr-Phe-Glu-Trp (SEQ ID NO:6) and Trp-Phe-Lys-Pro-Leu-Tyr (SEQ ID NO:7) which had been highly conserved in the known liquefying amylase derived from bacteria belonging to Bacillus sp. In each case, an amplified DNA fragment of about 1.0 kb was obtained. Subsequent to the analysis of the nucleotide sequence of the DNA fragment, the nucleotide sequences of the DNA fragment on the upstream side and downstream side which had been obtained by the reverse PCR method [T. Triglia, et al., Nucleic Acids Res., 16, 81(1988)] and a PCR in vitro cloning kit (product of Boehringer Mannheim GmbH) were analyzed. As a result, in an about 1.7 kb gene region of each of the strains, only one open reading frame (ORF) encoding 501 amino acid residues as shown in the Sequence Listing (SEQ ID NOS:2and 4) was found. It was elucidated that the sequence (Amino acid No. Asp 1 to Leu 15) in the amino terminal region completely conformed with the amino terminal sequence (15 amino acid residues) of Amylases K36 and K38 purified from the culture solution of the strains KSM-K36 and KSM-K38. The genes of the K36 and K38 amylases thus determined were found to have nucleotide sequences as shown in the Sequence Listing. (SEQ ID NOS:1and 3) respectively.

Example 10

By the PCR method with the chromosome DNA of each of the two strains as a template, a DNA fragment of 1.7 kb from the 0.7 kb upstream from the initiation codon to 0.1 kb downstream from the termination codon was amplified, followed by introduction into the strain *Bacillus subtilis* ISW 1214 by using a shuttle vector pHY300PLK (trade name; product of Yakult Honsha Co., Ltd.). The recombinant strain of the *Bacillus subtilis* thus obtained was subjected to liquid culture, whereby an amylase was produced in the culture solution. As a result of analysis of the properties of the amylase purified from the resulting culture supernatant by the method as shown in Example 3, it was revealed that they had good conformity with those of the amylase purified from the culture solution of each of the strains KSM-K36 and KSM-K38. Described specifically, the optimum acting pH was recognized to fall within a range of 8 to 9, the specific activity was about 4000 U/mg at pH 10 and resistance to each of a chelating agent and an oxidizing agent was high.

CAPABILITY OF EXPLOITATION IN INDUSTRY

Compared with the conventionally known amylases for a detergent, the liquefying alkaline amylases of the present invention have high chelating-agent resisting performance. Their optimum pH exceeds 8. The liquefying alkaline amylases according to the present invention can therefore be used in a markedly wide range of industrial fields, for example, in the step of processing a starch in an alkaline range. In particular, they bring about an advantage when incorporated in an automatic dish washing detergent, laundry detergent, bleaching agent or the like containing a chelating agent and thus possess industrially great significance.

What is claimed is:

1. An isolated liquefying alkaline amylase which has an amino acid sequence having a homology, calculated by the Lipman-Pearson method, of at least 80% with that shown in SEQ ID NO:2 or SEQ ID NO:4, and having residual activity not less than 70% when treated at pH 10 and 45° C. for 30 minutes in the presence of 1 to 100 mM of EDTA or EGTA.

2. The isolated liquefying alkaline amylase of claim 1, further: having an optimum acting pH exceeding 8.0; hydrolyzing α-1,4-glucosidic linkages in starches, amylose, amylopectin and partial degradation products thereof; forming glucose, maltose, maltotriose, maltotetraose, maltopentaose, maltohexaose, and maltoheptaose from amylose; and not acting on pullulan.

3. The isolated liquefying alkaline amylase of claim 2, further: exhibiting residual activity not less than 70% within a pH range of from 6.5 to 11.0 when treated at 40° C. for 30 minutes; acting in a temperature range of from 20 to 80° C.; and exhibiting residual activity not less than 80% at 40° C. when treated for 30 minutes in a 50 mM glycine-salt-sodium hydroxide buffer (pH 10).

4. The isolated liquefying alkaline amylase of claim 3, further exhibiting residual activity not less than 70% when treated at pH 10 and 30° C. for 60 minutes in the presence of 2% $H_2O_2$.

5. The isolated liquefying alkaline amylase of claim 1, which has the amino acid sequence of SEQ ID NO:2 or SEQ ID NO:4.

6. A detergent composition comprising an isolated liquefying alkaline amylase as claimed in claim 1.

7. A method for preparing a liquefying alkaline amylase which comprises inoculating a microorganism which is a Bacillus sp. strain KSM-K36 or KSM-K38 into an alkaline medium, incubating said microorganism to provide a culture, and collecting the liquefying alkaline amylase from said culture.

8. The product of the process which comprises inoculating a microorganism which is a Bacillus sp. strain KSM-K36 or KSM-K38 into an alkaline medium, incubating said microorganism to provide a culture, and collecting the liquefying alkaline amylase from said culture.

9. A method for preparing a liquefying alkaline amylase which comprises providing a vector plasmid containing SEQ ID NO:1 or SEQ ID NO:3, transforming a Bacillus sp. bacterium with the plasmid, incubating the transformed bacterium, and collecting the liquefying alkaline amylase from said culture.

10. The product of the process which comprises providing a vector plasmid containing SEQ ID NO:1 or SEQ ID NO:3, transforming a Bacillus sp. bacterium with the plasmid, incubating the transformed bacterium, and collecting the liquefying alkaline amylase from said culture.

* * * * *